(12) United States Patent
Bohlin (10) Patent No.: US 6,218,751 B1
(45) Date of Patent: Apr. 17, 2001

(54) BEARING DEVICE

(75) Inventor: Leif Bohlin, Sjobo (SE)

(73) Assignee: Global Hemostasis Institute MGR, Linkoping (SE)

( * ) Notice: Subject to any disclaimer, the term of this patent is extended or adjusted under 35 U.S.C. 154(b) by 0 days.

(21) Appl. No.: 09/424,225

(22) PCT Filed: May 26, 1998

(86) PCT No.: PCT/SE98/00985

§ 371 Date: Feb. 2, 2000

§ 102(e) Date: Feb. 2, 2000

(87) PCT Pub. No.: WO98/54475

PCT Pub. Date: Dec. 3, 1998

(30) Foreign Application Priority Data

May 26, 1997 (SE) .................................................. 9701959

(51) Int. Cl.[7] .......................... H02K 7/09; F16C 32/04; G01N 11/14
(52) U.S. Cl. ............................................. 310/90.5; 310/91
(58) Field of Search ..................................... 310/90.5, 91

(56) References Cited

U.S. PATENT DOCUMENTS

| | | | | |
|---|---|---|---|---|
| 2,305,416 | * | 12/1942 | Hansen | 310/90.5 |
| 2,747,944 | * | 5/1956 | Baermann | 310/90.5 |
| 3,114,582 | * | 12/1963 | Milligan | 310/90.5 |
| 3,614,181 | * | 10/1971 | Meeks | 310/90.5 |
| 3,761,148 | * | 9/1973 | Grosbard | 310/90.5 |
| 4,328,701 | | 5/1982 | Mau-Tung et al. | 73/59 |
| 5,506,459 | | 4/1996 | Ritts | 310/90.5 |

FOREIGN PATENT DOCUMENTS

| | | | |
|---|---|---|---|
| 3437937 A1 | 8/1985 | (DE) | G01N/11/14 |
| 3837845 A1 | 5/1990 | (DE) | F16C/32/04 |
| WO 9429692 A1 | 12/1994 | (WO) | G01N/11/14 |

OTHER PUBLICATIONS

Patent Abstracts of Japan, 7:202, JP 58–99727 A (Iwamoto Seisakusho K.K.), Jun. 14, 1983.

Derwent's Abstract, 89–322952/44, Abstract Of Su, 1455282 (Tomsk Univ. Appl. Mat), Jan. 30, 1989.

* cited by examiner

Primary Examiner—Burton Mullins
(74) Attorney, Agent, or Firm—Bacon & Thomas (57) ABSTRACT

Bearing device of magnet type for instruments and the like and non-contact support of one part relatively to another part by means of magnet fields wherein the one part is rotatable relatively to the other at least a part of a full turn. The novelty lies therein that the magnet devices intended to keep the rotatable part essentially centered relatively to the stationary part are off-set so that besides radially acting force components also axial force components biasing the rotatable part in an axial direction appear; and in that a connection device connecting the rotatable part with the stationary part and permitting the former to turn at least a portion of a turn is arranged along the axis of rotation so as to keep the rotatable part correctly off-set positioned.

14 Claims, 6 Drawing Sheets

BEARING DEVICE

TECHNICAL FIELD OF THE INVENTION

This invention relates to bearing devices with extremely low friction for the use for instance in Theological measuring devices and other sensitive instruments.

BACKGROUND OF THE INVENTION

In a known measuring instrument a movable instrument part is suspended by means of and between vertical tapes or strings with low torsion resistance and having low starting torque. The movable instrument part is to be influenced by the power, the effect or the like to be measured. The moving coil galvanometer is one example of such an instrument. Instrument parts suspended by tapes or strings may be used for instruments where the displaceable or rotatable part is influenced or biased without physical contact, i.e. without mechanical influence from another part. For purposes where the object to be tested or otherwise analysed is to be physically attached to the movable part or where an indicating device or the like is to be mechanically connected to a transmitter the known arrangements are hardly usable.

It has been suggested to use—for bearings where low friction and low starting torque is required—different types of magnetic bearings. DE 34 37 937 discloses a such device and more in detail a device for guiding and supporting rheological measuring systems. The intention was to bring about, in a simple way, a guiding and supporting arrangement with minimum friction and based on one stationary and one mobile magnet system with a soft iron part arranged with a vertical air gap.

Already in the 19th century however it was proved by a Mr. EARNSHAW that a devices like the one according to the DE publication is functionally impossible because of their inherent instability. It is physically impossible to achieve stability both axially and radially as is maintained in the DE publication. The device according to the DE publication not only has inferior lateral stability but is also unstable which means that it will collapse and loose its position either at the upper or the lower pair of magnets immediately.

To further clarify the state of the art and to define the invention over the state of the art, it must be mentioned that the invention is based primarily on passive magnet systems including permanent magnets only. Active magnet bearings include electromagnets shaped and arranged in a way very similar with the arrangement of a stator of a synchronous motor, whereas the armature or rotor normally is formed by a circular package of transformer sheet metal. The position of the rotor is read and checked by means of a number of distance sensors the signals from which via a quick acting boost control system optimises and distributes signals to each of the amplifier each controlling an electromagnet. In this way the rotor and shaft can be easily re-set and guided to its intended position. Annular magnet bearings, often called passive magnet bearings include annular shaped permanent magnets which attract alternatively repel each other in such a way that stability is achieved in one desired direction only, radially or axially. In the other direction, however, the bearing will always be unstable, a fact which was proven more than a hundred years ago. If ever utilized, this type of bearings always is used together with an auxiliary bearing such as an active magneto bearing.

ASPECTS ON THE INVENTION

One purpose with the invention is to bring about, by utilising a passive magnet system having a minimum of frictional resistance, an axially and radially stable bearing device especially but not exclusively for instruments of rheometer type.

SUMMARY OF THE INVENTION

The invention is a bearing device for passively supporting one part movable relatively to another part by means of magnets, preferably permanent magnets in order to bring about a stable essentially friction free measuring of a torque in a range where conventional bearing systems of the instrument ball bearing type or the like have too high a friction and too high a starting torque and the characterising features of the invention lies in that at one part and at another part, the one part rotatable relatively to the other part at least part of a revolution, pairs of magnet units arranged in a repulsion or attraction state are positioned regarding their fields of force in such a way that force components hold the rotatable part in a predetermined radial position and bias the rotatable part in an axial direction and in that at least one mechanical, essentially stable positioning means is connected between the one part and the other part and acting along the axis of rotation for counterbalancing the force biasing the one part in the one axial direction.

BRIEF DESCRIPTION OF DRAWINGS

In the following the invention will be described more in detail with references to the attached drawing, in which.

DETAILED DESCRIPTION OF PREFERRED EMBODIMENTS

As an example of field of use has been selected viscosimeter especially such ones for rheometer purposes and the viscosimeter is in the drawings symbolised by a vessel marked K. The viscosimeter are very schematically illustrated and the purpose is to establish that a measuring is to take place with a medium inside the vessel K enclosing and surrounding a central measuring body M. The bearing device naturally can be used for other types of instruments with rotational movements less than a full circle.

In all the embodiments shown, there is at least one pair of magnet units including one stationary magnet unit 1 and at least one movable magnet unit 2 and the magnet units are concentrically arranged relatively to an axis around which one instrument part is rotatable. The shown magnets units have all permanent magnets, but it is theoretically possible to replace the magnets of the one pair with electromagnets. Normally several pairs of magnet units cooperate with each other.

The stationary magnet units 1 are arranged or affixed at a stationary part, such as a support or stand 3 only schematically shown, whereas the movable magnet units 2 are arranged at or affixed to a rotatable part, such as a body or spindle rotatable relatively to the support or stand 3. The two parts are connected by means of a connector 5 permitting relative rotation over at least part of a revolution and the purpose of this will be further discussed below.

The pairs of magnet units 1 and 2 and their fields of force are so arranged relatively to each other that by means of the interaction the one or rotatable part 4 is kept centred relatively to the other or stationary part 3. This can be reached by means of repulsion of attraction. On arranging any pair of magnet units to interact there exists between the interacting fields of force—in a defined relative position—a so called null point, i.e. a relative position where a sort of equilibrium prevails. This equilibrium, however, is extremely unstable and even a tiny mechanical disturbance causes the interaction to collapse resulting in an displacement of the relative positions of the parts involved.

According to this invention the interacting magnet units with their fields of force are positioned relatively to each other off-set from the null point, meaning that there appear, besides the essentially radial force components working for mutually repulsing or attracting the parts, i.e. keeping the rotatable part centred relatively to the stationery part, also axial force components which bias the rotatable part in the one axial direction or the other, depending on in which direction relatively to the off-set point the parts are displaced. By arranging between the one or rotatable part 4 and the other or stationary part 3 the connector means 5 the axial biasing force is counterbalanced and the position of the rotatable part, both radially and axially relatively to the stationary part remains stable.

The connector means shown in FIGS. 1–4 is a so called torsion means, viz. a string or tape which allows rotation over at least part of a revolution and normally several revolutions with a minimum resistance.

It is also possible to use, in stead of the torsion means, string or tape taking up a tensional force, a connector means including low friction material co-operating with a pin or seat, i.e. a watch type bearing including pieces of hard materials such as diamond, ruby, sintered carbide or steel and co-operating pin or seat devices of appropriate material. In this case the connection is subject to a pressure instead of a tension as with the torsional means.

Figure 1:
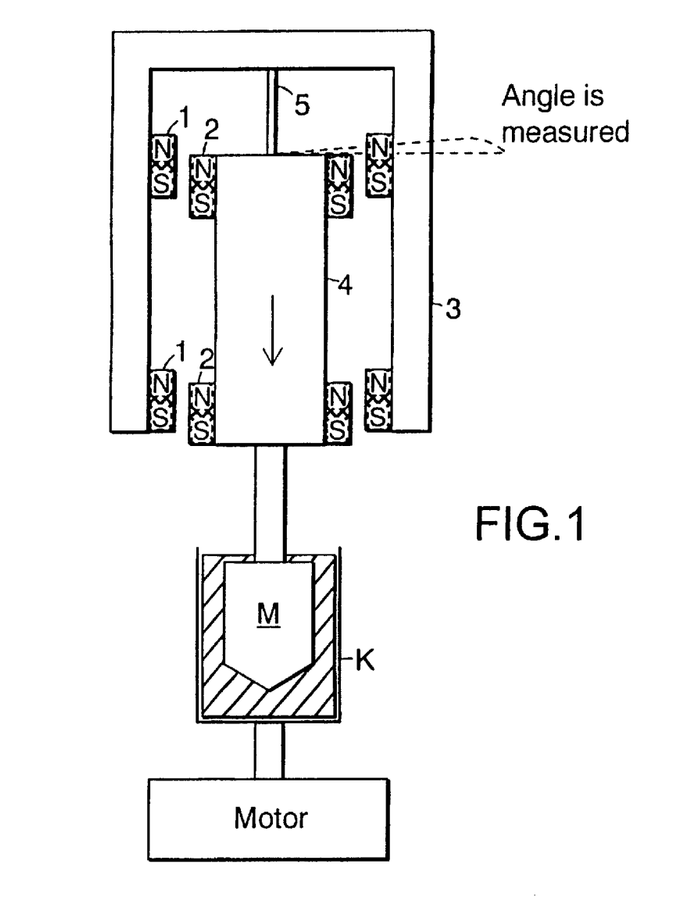
FIG. 1 is a schematically axial section showing one embodiment of the bearing device with passive magnet bearings utilised for a viscosimeter of Couette type.

In the embodiment shown in FIG. 1 the viscosimeter is of Couette type and includes a the vessel K supported by a motor shaft and the measuring body M is to be dipped into the liquid inside the vessel. The measuring body M is rigidly connected to the spindle 4. The magnets of this embodiment are concentrically arranged and axially magnetised. Consequently the co-operation between the magnets or rather the repulsion forces try to push the spindle downwardly causing a tension in the torsion string 5. The string however prevents any axial displacement of the spindle 4 and the result is that a balance is reached and the spindle is held exactly in the centre of the device.

Figure 2:
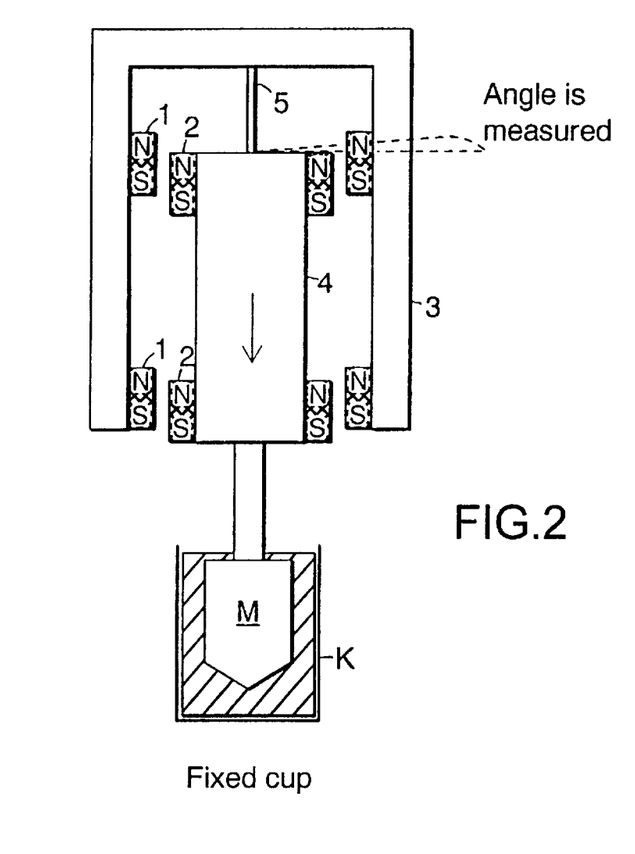
FIG. 2 is a schematically axial section of an embodiment with a passive magnet bearing device utilised for an oscillating viscosimeter.

The embodiment according to FIG. 2 differs from the one according to FIG. 1 in that there is no motor for rotating the vessel K, but otherwise the interaction between the magnets and the string is equal with that of FIG. 1.

Figure 2B:
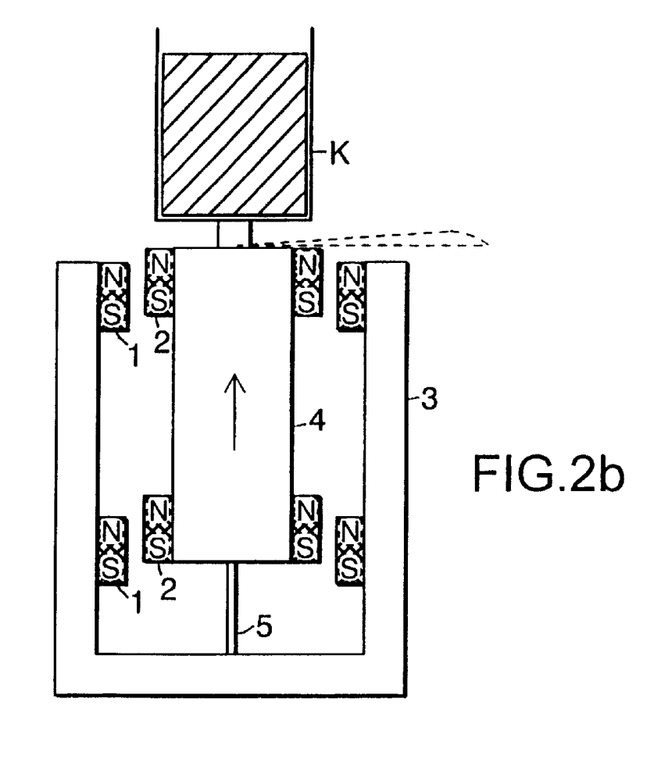
FIG. 2b is a schematically axial section through an embodiment with a passive magnet bearing device arranged with axially magnetised concentric magnets for a viscosimeter having including a cup, FIG. 2c in an axial section shows an oscillating viscosimeter with only a cup and an embodiment of a passive magnet bearing arranged with radially magnetised concentric magnets.

FIG. 2b shows another embodiment, and in this the magnets are arranged in a way similar to that of FIGS. 1 and 2 but the support and spindle arrangement is inverted. Consequently the magnets of the support and of the spindle act in the opposite direction and strive for lifting the spindle out of the support. The torsion string 5 prevents any axial movement upwardly of the spindle and the cooperating magnets of the support and the spindle create a stabilising force.

Figure 2C:
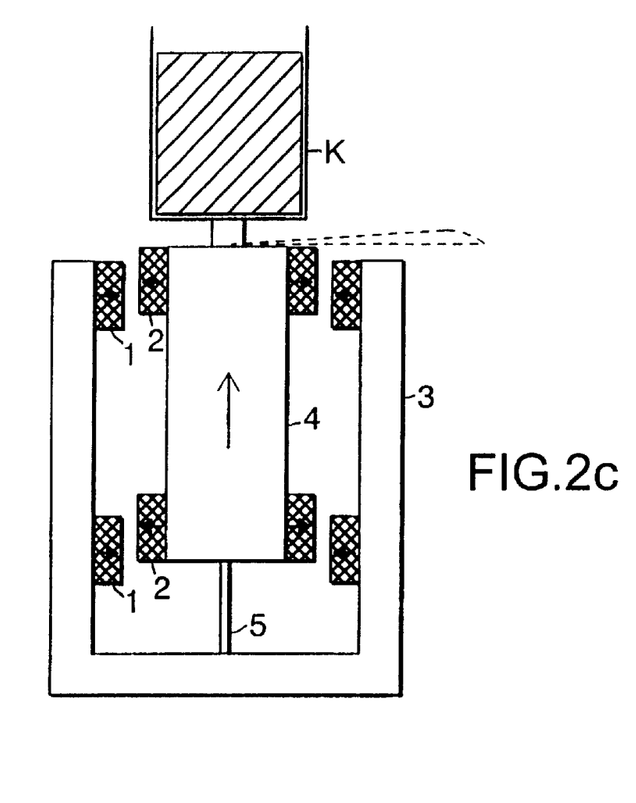

FIG. 2c differs form the just described embodiment in that the magnets are radially magnetised. The magnets 1 of the support are directed magnetically in a direction opposite to that of the magnets 2 of the spindle 4. The magnets 1 and 2 of FIG. 2c try to repel each other but as the support does not give way outwardly and the spindle does not give way inwardly the combined forces result in a position of equilibrium, which per se is unstable, but as the magnets 1 and 2 are mutually axially offset there appear an axial force component trying to axially displacing the spindle 4 relatively to and out of the support 3. This lifting force is counteracted by the unyielding torsion string 5 and the result is that the spindle is kept stable in the centre of the support in a position defined both radially and axially.

Figure 3:
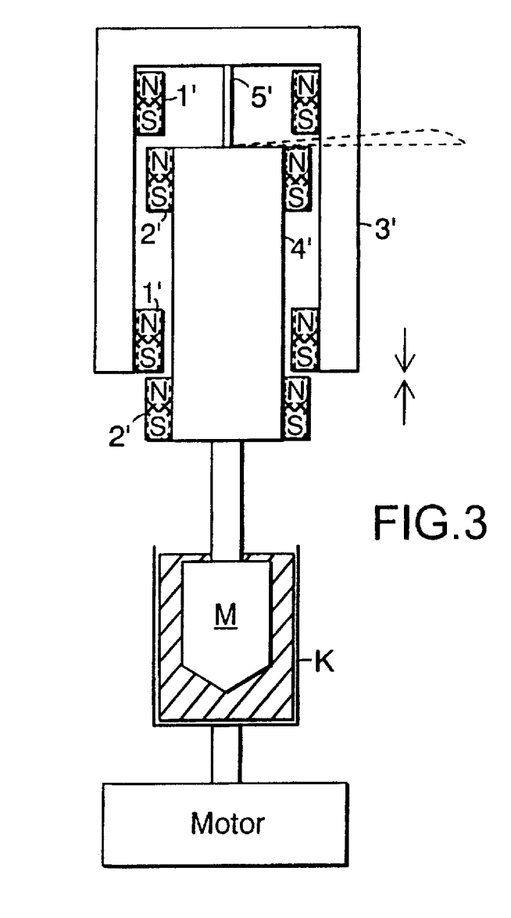
FIG. 3 shows in an axial cross section a viscosimeter of Couette type with repulsive magnet bearings with passive magnets arranged in a parallel state, FIG. 4 in a same way illustrates an oscillating viscosimeter with an attractive passive magnet bearing with the magnets arranged in parallel, and FIG. 5 schematically shows ten different configurations with combinations of radially and axially magnetised magnetos acting as a radial magneto bearing, FIG. 6 schematically partly in cross section shows a Theological instrument with a bearing according to the invention.

In FIG. 3 is illustrated an embodiment utilised at a viscosimeter of Couette type, i.e. similar with the viscosimeter according to FIG. 1, but the magnets 1' of the support 3' and the magnets 2' of the spindle 4' are arranged in an axial arrangement. The magnets 1' and 2' are axially displaced and otherwise so oriented that the magnet poles are in a repulsion state. The stationary magnets 1' try to push the spindle with the movable magnets 2' out of the support 3' but this is counteracted by the string 5' connecting the spindle 4' to the support 3' thereby keeping the spindle in an axially defined position as well as in a radially well defined position.

Figure 4:
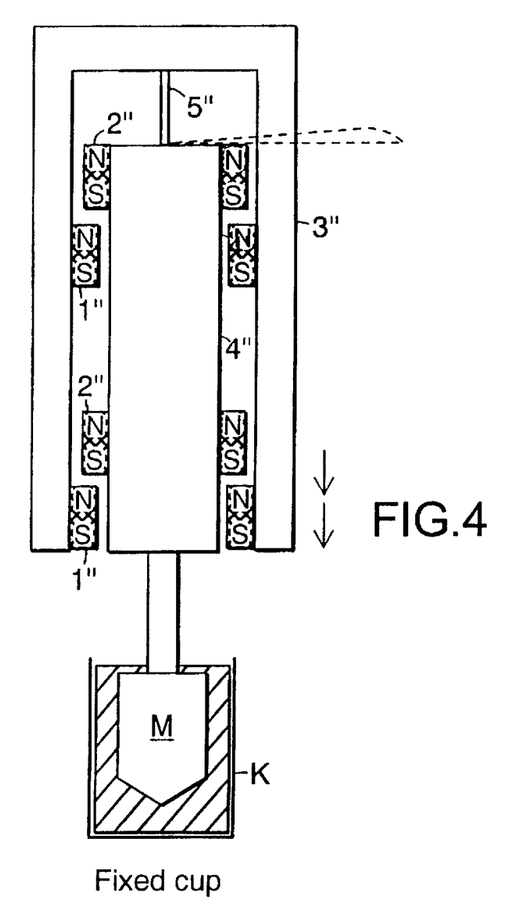

The embodiment according to FIG. 4 illustrates a viscosimeter comparable with the one according to FIG. 2 but as in the embodiment according to FIG. 3 the magnets are arranged in an other way than in the embodiment according to FIG. 2. According to FIG. 4 the magnets 1" and 2" are arranged in parallel with each other and axially displaced. In this case however the poles of the magnets are arranged in a way opposite to that according to FIG. 3, namely so that the stationary magnets 1" try to attract the movable magnets 2" and so to say try to pull the spindle 4" out of the support 3". As in the other examples the torsion string 5" counteracts the axial displacing of the spindle.

The examples given in FIGS. 1 to 4 are the once now preferred especially for instruments of the type shown.

Figure 5:
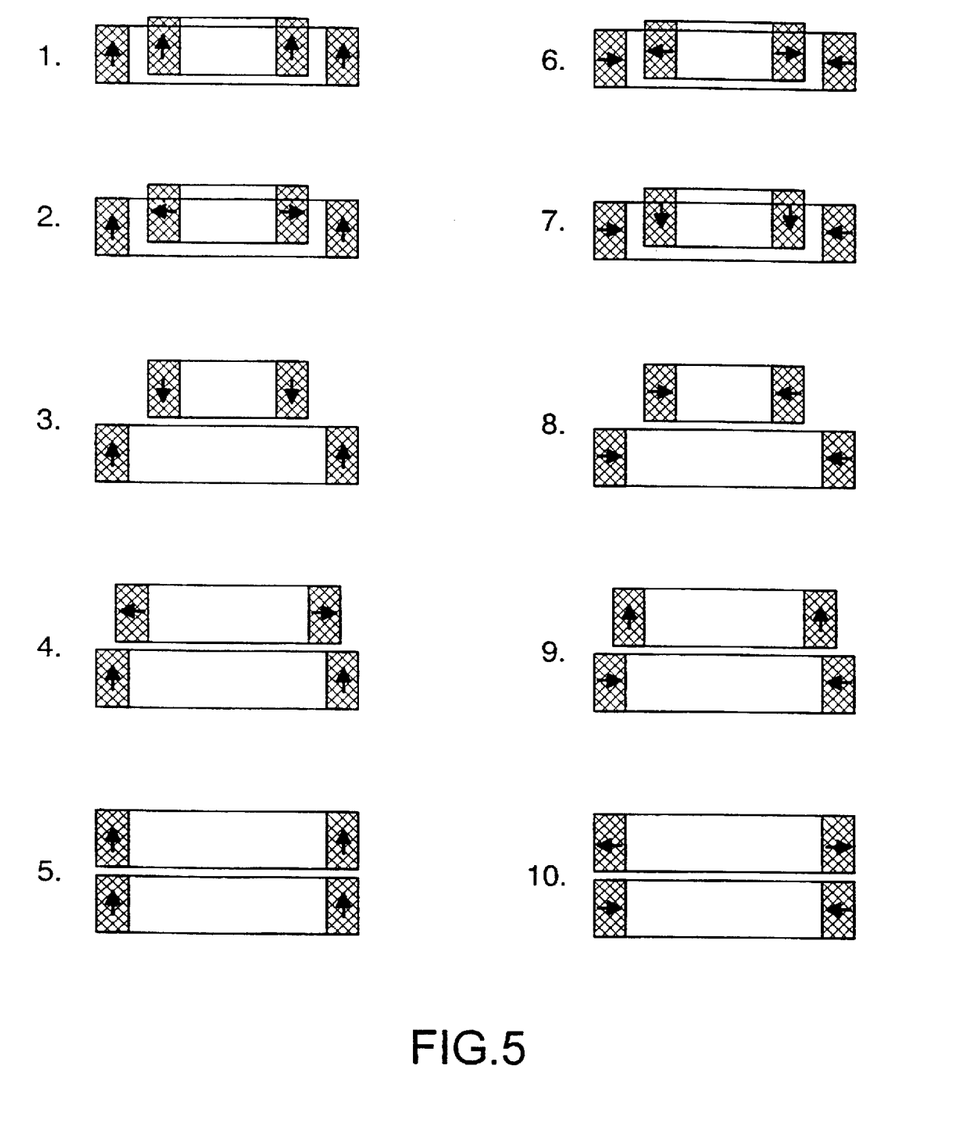

FIG. 5 schematically shows no less than ten different configurations with combinations of radially and axially magnetised magnets for radial passive magnet bearing devices, which can be used for the bearing device according to this invention. In FIG. 5 no connecting means are shown as the positioning of said devices depends on the selected off-set direction and the type of connecting device chosen.

Item one is a combination with axially magnetised magnets and it is clearly visible that the inner and outer magnets are mutually offset in axial direction.

Item two is combination of axially and radially magnetised magnets.

Item three is a combination of opposing axially magnetised magnets where the movable magnets are axially displaced relatively to the stationary ones.

Item four is an other example of magnets magnetised similar with the ones of item two but where the movable magnets are placed beyond the stationary ones.

Item five is an arrangement similar to the one according to FIG. 4 that is with attractive arrangement of the magnets.

Item six shows an arrangement with oppositely directed radially magnetised magnets.

Item seven shows the opposite to item two that is the movable magnets are axially magnetised whereas the stationary ones are axially magnetised.

Item eight is an example where the movable and the stationary magnets are magnetised unidirectional.

Item nine is comparable with item seven but the movable magnets are magnetised in opposite directions and positioned beyond the stationary ones.

Item ten is comparable with item six but in this case the stationary and the movable magnets are acting in different axial planes.

Figure 6:
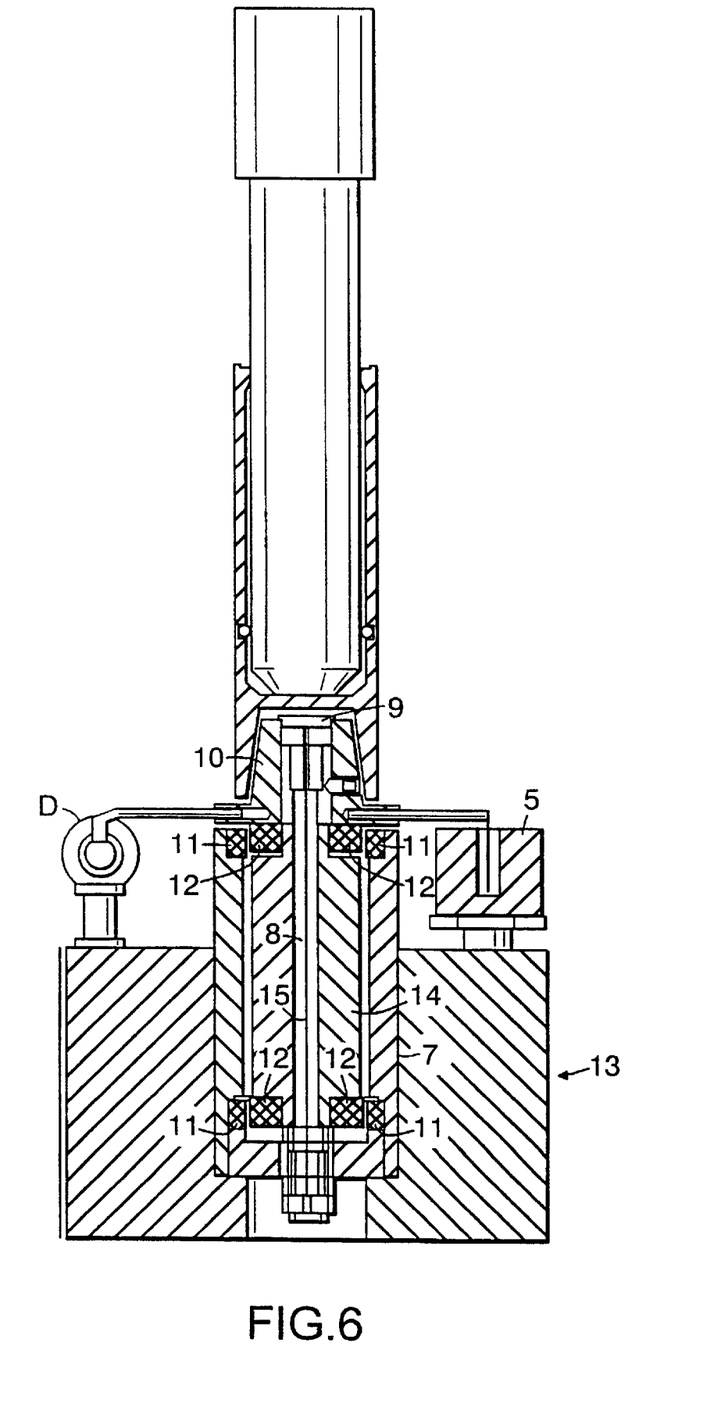

The embodiment according to FIG. 6 includes a support or stand 13 in which a vertical bore 7 is arranged. Around the bore 7 there are stationary magnets 11 and inside the bore 7 a spindle device 14 carrying a number of magnets 12 co-operating with the stationary magnets 11 of the stand 13. The spindle 14 is provided with a central bore 8 and has at its upper end projecting above the stand a connection 9 for a torsion string or wire 15 extending along the central bore of the spindle and so adapted that the spindle is kept in a defined axial position relatively to the stand by the influence of the magnets 11 and 12, respectively, at the stand and the spindle so that the resulting force strives to push the spindle upwardly, i.e. out of the bore of the stand. The torsion wire this way will determine the axial position and create a stabilising force holding the spindle in the centre of the stand bore 8.

At its upper end the spindle 14 has a conical head 10 adapted to be received in a complementary shaped recess R of a measuring vessel carrier or holder.

The spindle 4 in the illustrated embodiment is provided with a driving means D adapted to give the spindle a controlled limited rotational movement and a sensor means S also connected to the spindle and influencing a computer device for determining the properties of a liquid filled into the vessel K.

As a torque resistance of the torsion string or wire 5 is known and constant and also the force exerted by the driving means it is by means of the sensing device in co-operation with the computer possible to determine the properties of the liquid in the vessel.

The embodiments discussed above are generally intended for instruments and the like where the rotatable part rotates over a fraction of a turn or just a few turns. As mentioned above it is however possible to utilise a torsion means, a string or the like which allows a large number of rotations if this is required. If the device is intended for a use where the rotatable part is intended to rotate many turns, the axial positioning against the axial thrust from the co-operating magnetos, normally is reached by means of an axial bearing e.g. of watch spindle type, where a pin is received in a recess in a piece of a hard material such as diamond, ruby, sintered carbide or the like or of the type where a spherical body attached to the one part is received in a part spherical seat at the opposite part. Such axial bearings, similar with the torsion string or tape, naturally, are localised in such a way that the rotational axis thereof is congruent with the rotational axis of the bearings device as a whole. In the axial bearing types the bearing is subjected to an axial thrust or pressure, the contrary to the torsion means types where a tensional force acts along the torsion means.

Figure 7:
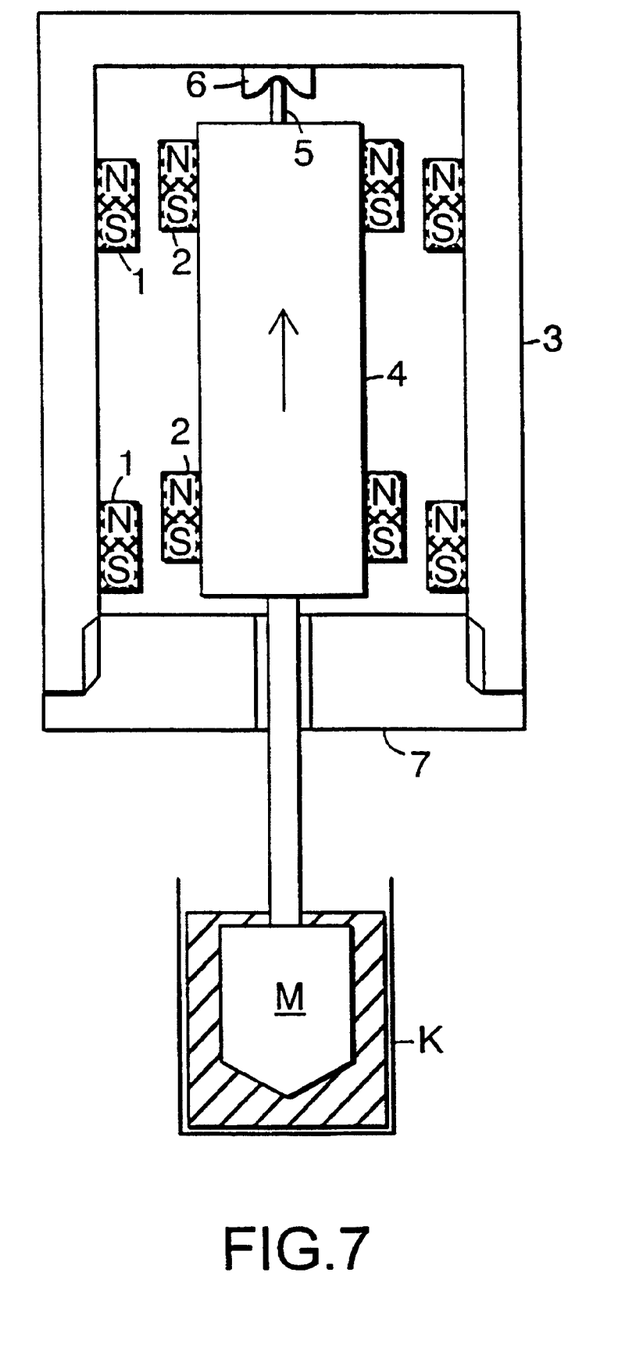
FIG. 7 is a longitudinal sectional view of a further embodiment.

The embodiment according to FIG. 7 shows one example of a device where there is no torsion means but instead a pin 5x cooperating with a bearing piece 6x of saphire, ruby, diamond or the like hard material. The magnets are magnetised in such a way that the axial force component thereof pushes the inner part 4 upwardly towards the bearing piece 6x. The pin being rather weak has as only purpose to stabilize the inner part 4 axially. From the same figure can also be seen a holed lid like lid like ond closure of the outer part 7 serving as an abutment preventing accidental axial movements of the inner part.

In the embodiments shown there are at least two pairs of magnet units, axially separated from each other. By arranging two sets of axially spaced magnet units as disclosed radial aligning or stability is achieved. If there was only one set of magnet units the rotatable part could have a tendency to rock or swing, meaning that the axis of rotation would deviate and rotate around the intended geometrical axis. By arranging two axially spaced magnet sets the axis of rotation is stabilized and kept aligned with the geometrical axis.

The magnet units in each set can be similarity oriented magnetically, i.e. so that they bias the rotatable part together in the same direction. They can, however, also be oriented opposite to each other so that they bias the rotatable part in opposite directions. In the lafter case, it is important that the biasing force of the one set of magnet units overrides the biasing force of the other set of magnet units and this is a necessity both in the case the units work inwardly against each other or outwardly from each other. In order to keep the rotatable part in its intended position, there is, according to the invention, arranged a connector means which positions the rotatable part either by means of a torsion device or an pin bearing against a hard material or the like.

In instruments where a rotatable part is supported by a connector especially by a torsion string balancing the axial force from the magnet units, the rotatable part 3 could by accident be pushed inwardly so that it not only reaches the null point but also passes this equilibrium position. The result would be a total wrecking of the instrument. In order to reduce the risk for such accidents it is suggested to arrange a second connector means acting in a direction opposite to the one of the first connector means and this means could be of torsion means type or hard material bearing type. The most convenient way is to attach one connector means at each axial end of the rotatable part but is in many cases more convenient to arrange at the one axial end only of a rotatable part, a combined torsion string and hard material bearing by mounting the string inside a tube like device at either end having a seat or surface co-operating with a hard material piece. In this way the opposite end of the rotational part is free for attaching measuring vessels or the like.

To reduce the risk for, by mistake, pushing the rotatable part so that it passes the null point and disappears into the stationary part, it is also possible to arrange mechanical abutments either at the stationary or the rotatable part or at both and design the abutments so that the rotational part after a small axial displacement is prevented from entering the stationary part alternatively to leave the stationary part if the connector means fails.

What is claimed is:

1. A magnetic bearing device for use in instruments and which allows a rotational movement of a first part relative to a second part and including at least one magnet unit at each of the parts, said magnet units creating magnetic fields, the forces of which stabilize the parts relative to each other including in directions radial to the axis of rotation of the first part, wherein the magnet unit or units (2) of the first, rotatable, part (4) is so localized and arranged relative to the magnet unit or units (1) of the second, stationary, part (3) that the interacting fields of force of the magnet units (1,2) of the two parts create both radially acting stabilizing force components and force components resulting in an axial displacement force biasing the first, rotatable, part (4) in the one axial direction relative to the second, stationary, part (3), and wherein at least one axially acting mechanical positioning means (5) is mounted to connect the first part with the second part, said positioning means counteracting the axial force component biasing the first rotatable part and being at least in one direction axially stable, at least partially rotatable connector, wherein the connector is a torsion means (5) secured to the first rotational part at and extending along the rotation axis thereof, said torsion means allowing at least limited rotation in either rotational direction and preventing displacement in at least the one axial direction caused by the axial repelling force component.

2. A bearing device according to claim 1, wherein the torsion means is a torsion wire.

3. A bearing device according to claim 1, wherein the torsion means is a torsion string.

4. A bearing device according to claim 1, wherein there are torsion means attached at each axial end of the first, rotatable, part and extend axially outwardly therefrom to appropriate securing points on the second, stationary, part, one of the torsion means preventing axial displacement of the rotatable part in a direction opposite to the displacement preventing direction of the other torsion means.

5. A bearing device according to claim 1, wherein mechanical axial displacement preventing abutment portions are arranged at at least one of the first and the second part, said portions upon engagement preventing the displacement of the rotatable first part relative to the stationary second part beyond a minimum displacement.

6. A bearing device according to claim 1, wherein each magnet unit includes a number of axially magnetized magnets (2).

7. A bearing device according to claim 6, wherein the magnets are concentrically arranged.

8. A bearing device according to claim 1, wherein each magnet unit includes a number of radially magnetized magnets.

9. A bearing device according to claim 8, wherein the magnets are concentrically arranged.

10. A bearing device according to claim 1, wherein the first part and the second part (4, 3) are provided with axially in both directions facing abutment portions preventing axial displacement beyond a pre-set distance in both axial directions.

11. A bearing device according to claim 1, wherein at least two axially spaced sets of magnets (2, 1) are arranged at the first, rotatable, part (4) as well as at the second, stationary, part (3), the magnetic force fields thereof being arranged to give an excess of axial biasing force in the one direction, this excess force being counterbalanced by the mechanical positioning means (5).

12. Analyses instrument comprising a bearing device according to claim 1.

13. A method for determining rheological properties of a liquid, comprising placing the liquid in a vessel (K) of an analysis instrument according to claim 12 and recording and analyzing the readings of the instrument.

14. A method according to claim 13, the analysis is performed by means of a computer program.

* * * * *